United States Patent [19]

Lin et al.

[11] Patent Number: 5,145,967
[45] Date of Patent: Sep. 8, 1992

[54] METHOD FOR PREPARING 4-ALKOXYALKYL-4-PHENYLAMINOPIPERDINES AND DERIVATIVES THEREOF

[75] Inventors: Bor-Sheng Lin, Berkeley Heights; H. Kenneth Spencer, Chatham; Joseph W. Scheblein, Flemington, all of N.J.

[73] Assignee: Anaquest, Inc., Libery Corner, N.J.

[21] Appl. No.: 608,427

[22] Filed: Nov. 2, 1990

Related U.S. Application Data

[63] Continuation-in-part of Ser. No. 340,976, Apr. 20, 1989, abandoned.

[51] Int. Cl.$^5$ .............................................. C07D 401/04
[52] U.S. Cl. ..................... 546/208; 546/187; 546/190; 546/191; 546/193; 546/194; 546/196; 546/197; 546/198; 546/199; 546/200; 546/201; 546/202; 546/209; 546/210; 546/211; 546/212; 546/213; 546/223; 546/224; 544/323; 544/326; 544/324; 544/227; 544/284
[58] Field of Search ............... 546/223, 224, 194, 202, 546/208, 209, 213, 196, 199, 200, 201, 190, 191, 187, 193, 197, 210, 211, 212; 544/323, 326, 329, 277, 284, 324

[56] References Cited

U.S. PATENT DOCUMENTS

| | | | |
|---|---|---|---|
| 3,164,600 | 1/1965 | Jannsen | 546/223 |
| 3,998,834 | 12/1976 | Jannsen et al. | 546/207 |
| 4,584,303 | 4/1986 | Huang et al. | 546/207 |
| 4,791,120 | 12/1988 | Lin et al. | 546/194 |

OTHER PUBLICATIONS

J. March, "Advanced Organic Chemistry", 2nd ed., p.666, McGraw-Hill, New York (1977).
E. E. Smissman et al., *J. Org. Chem.*, "Thiomethylation", 35 (5), 1357-1360 (1970).
C. G. Gutierrez et al., *J. Org. Chem.*, "Tri-n-Butyl Tin Hydride", 45 (17), 3393-3395 (1980).
V. H. Rawal et al., *Synthetic Communications* 14, (1984), pp. 1129-1139.
A. H. Becket et al., *J. Med. Pharm. Chem.*, vol. 1, (1959), pp. 37-58.
C. R. Ganellin et al., *J. Med. Chem.*, vol.8, (1965), pp. 619-625.
P. M. Carabateas et al., *J. Med. Pharm Chem.*, vol. 5, (1962), pp. 913-919.
P. Van Daele et al., *Arzneim-Forsch. Drug Res.*, vol.26, (1976), pp. 1521-1531.
R. A. Olofson et al., *J. Org. Chem.*, vol. 49, (1984), pp. 2081 / 2082.

Primary Examiner—Richard L. Raymond
Assistant Examiner—Mark W. Russell
Attorney, Agent, or Firm—R. Hain Swope; Larry R. Cassett

[57] ABSTRACT

The present invention is directed to a method for preparing a 4-alkoxyalkyl-4-phenylaminopiperidine compound which comprises the steps of (a) reacting an N-substituted-4-piperidone compound with an aniline compound to form a Schiff base compound, (b) reacting the Schiff base compound with an anionic reagent having an anion stabilizing group to form an amine compound, and (c) reducing the amine compound in step (b) with a reducing agent to displace the anion stabilizing group.

The anionic reagent in step (b) above has the general formula:

$$X-CYM-Z$$

wherein X is an anion stabilizing group, Y is hydrogen or lower-alkyl, Z is lower-alkoxy or phenylmethoxy, M is an alkali or alkaline earth metal, and C is a carbon atom.

6 Claims, No Drawings

METHOD FOR PREPARING 4-ALKOXYALKYL-4-PHENYLAMINOPIPERDINES AND DERIVATIVES THEREOF

RELATED APPLICATIONS

This application is a continuation-in-part of U.S. patent application Ser. No. 07/340,976, filed Apr, 20, 1989, now abandoned.

The present invention relates to a method for preparing 4-alkoxyalkyl-4-phenylaminopiperidines and N-phenyl-N-(4-alkoxy-alkylpiperidin-4-yl) amides and derivatives thereof, useful as intravenous analgesics or anesthetics.

BACKGROUND OF THE INVENTION

A number of patents disclose certain N-phenyl-N-(4-alkoxyalkylpiperidin-4-yl)amides having therapeutic activity. For example, Janssen et al. U.S. Pat. No. 3,998,834 discloses certain N-phenyl-N-[(N-heterocyclic) piperidin-4-yl]amide compounds, useful as analgesics, having a 4-lower-alkoxy methyl substituent on the piperidine ring. Huang et al. U.S. Pat. No. 4,584,303 also discloses certain 4-alkoxyalkyl-substituted N-phenyl-N-[(N-heterocyclic)piperidin-4-yl]-amide compounds, useful as analgesics, having a 4-lower-alkoxy methyl substituent on the piperidine ring.

The 4-lower-alkoxy methyl piperdone ring substituent in these prior art compounds is introduced by reacting an appropriately N-substituted-4- piperidone compound with an appropriately substituted aniline compound and an alkali metal cyanide. The resulting nitrile derivative is then hydrolyzed to the corresponding amide, which in turn is hydrolyzed to the corresponding acid, which is then esterified, reduced with a hydride reagent to the corresponding alcohol, and subsequently O-alkylated.

Janssen, U.S. Pat. No. 3,164,600, discloses a process wherein N-benzylpiperidone is reacted with an arylamine to form a Schiff base compound which is reacted with an alkyl lithium to yield a 4-alkylpiperidine derivative. This method produces the desired alkylpiperidine compounds in low yields.

V. H. Rawal et al. disclose the use of the alpha-lithium derivative of methoxymethyl phenyl sulfide, [(methoxymethyl)-thio]benzene, as a synthetic reagent useful in adding to certain compounds containing a carbonyl group, a halide group, or an epoxide group, as well as to certain compounds containing a nitrile group, an amide group, or an acid chloride group, to form the corresponding acyl derivative compound, Synthetic Communications. 14, 1129-1139 (1984).

SUMMARY OF THE INVENTION

The present invention is directed to an efficient method for preparing an 4-alkoxyalkyl-4-phenylaminopiperidine compound which comprises the steps of (a) reacting an N-substituted-4-piperidone compound with an aniline compound to form a Schiff base compound, (b) reacting the Schiff base compound with an anionic reagent having an anion stabilizing group to form an amine compound, and (c) reducing the amine compound in step (b) with a reducing agent to displace the anion stabilizing group.

The anionic reagent in step (b) above has the general formula:

X—CYM—Z wherein X is an anion stabilizing group, Y is hydrogen or lower-alkyl, Z is lower-alkoxy or phenylmethoxy. M is a metal atom selected from the group consisting of alkali and alkaline earth metals, and C is a carbon atom.

DETAILED DESCRIPTION OF THE INVENTION

The present invention is directed to a method for preparing a 4-alkoxyalkyl-4-phenylaminopiperidine compound which comprises the steps of (a) reacting an N-substituted-4-piperidone compound with an aniline, i.e. an aminophenyl, compound to form a Schiff base compound, (b) reacting the Schiff base compound with an anionic reagent containing an anion stabilizing group to form an amine compound, and (c) reducing the amine compound with a reducing agent to displace the anion stabilizing group.

In a preferred embodiment, the present invention is directed to a method for preparing 4-alkoxyalkyl-4-phenylaminopiperidine compounds and N-phenyl-N-(4-alkocyalkylpiperidin-4yl)amide derivatives having the general formula:

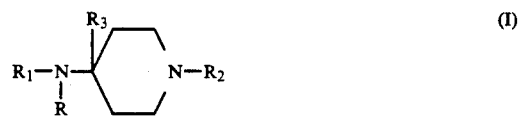

including optically active isomeric forms, wherein R is phenyl or substituted phenyl; $R_1$ is selected from the group consisting of hydrogen, lower-alkyl carbonyl, lower-alkenyl carbonyl, lower-alkoxy lower-alkyl carbonyl and cycloalkyl carbonyl; $R_2$ is selected from the group consisting of hydrogen, lower-alkyl, cycloalkylmethyl, phenyl lower-alkyl, and heterocyclic ring system lower-alkyl; and $R_3$ is lower-alkoxy lower-alkyl or phenylmethoxy lower-alkyl.

Several convenient routes for the preparation of the compounds which may be prepared by the method of the present invention begin with the known piperidone starting materials shown below:

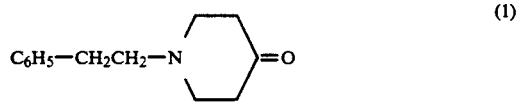

or

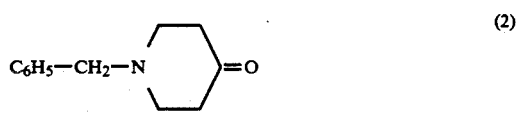

Compound (1), N-(2-phenylethyl)-4-piperidone, can be prepared according to the procedure published by A. H. Becket, A.F. Casey and G. Kirk, *J. Med Pharm. Chem.*, Vol. 1p. 37 (1959). Compound (2), N-phenylmethyl-4-piperidone, can be prepared in an analogous manner by the procedure described by C. R. Ganellin and R. G. Spickch, *J. Med. Chem.*, Vol. 8, p. 619 (1965) or P. M. Carabateas and L. Grumbach, *J. Med. Pharm. Chem.*, Vol. 5, p. 913 (1962).

In one example of the method of the present invention, an N-substituted-4-piperidone compound, such as N-(2-phenylethyl)-4-piperidone (1), is reacted with aniline, or a substituted aniline, to form a Schiff base compound (3).

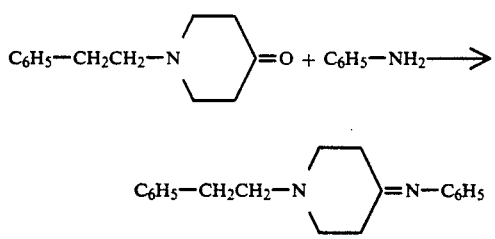

The Schiff base compound (3) is then reacted with an anionic reagent (4) having the general formula:

X—CYM—Z       (4)

wherein X is an anion stabilizing group, Y is hydrogen or lower-alkyl, Z is lower-alkoxy or phenylmethoxy, M is a metal atom selected from the group consisting of alkali and alkaline earth metals, and C is a carbon atom.

The Schiff base compound (3) and anionic reagent (4), such as the alpha-lithium derivative of methoxymethyl phenyl sulfide, react to form compound (5) 4-phenylamino-4-(1-thiophenyl-1-methoxymethyl)-N-(2-phenylethyl) piperidine.

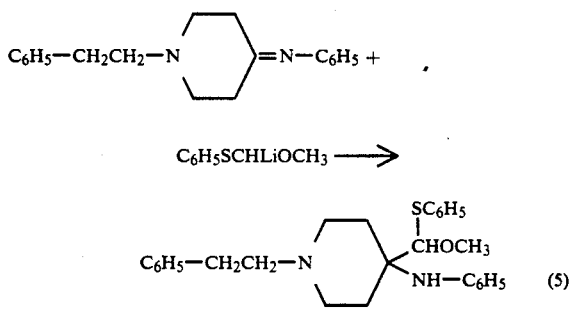

Amine compound (5) is then reduced with a suitable reducing agent, for example, n-tributyltin hydride, to displace the thiophenyl anion stabilizing group and yield 4-phenylamino-4-methoxymethyl-N-(2-phenylethyl)piperidine (6).

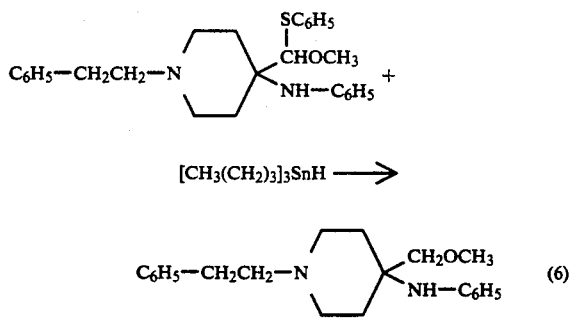

Compound (6) can be reacted with an appropriate acid halide (e.g., $R_4COCl$) or an anhydride, e.g., $(R_4CO)_2O$ wherein the expression "$R_4CO$—" equals $R_1$ as defined above to introduce the desired $R_1$ group on the nitrogen atom and thereby obtain compound (I), according to the reaction scheme shown below:

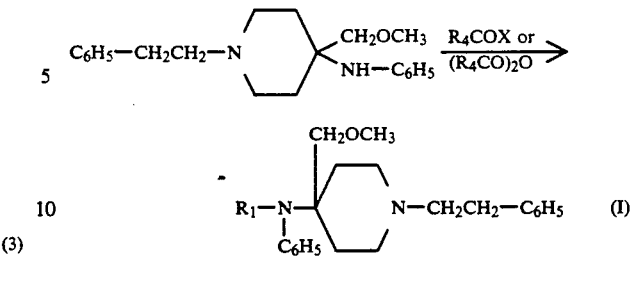

wherein $R_1$ is set forth above.

The anionic reagent of the present invention has the general formula:

X—CYM—Z       (4)

therein X, Y, Z, M and C are defined as set forth below:

In Formula 4, X is an anion stabilizing group, i.e. an electronegative group which can stabilize a negative charge on the adjacent carbon atom C such that carbon atom C can add to Schiff base compounds of Formula (3). Suitable anion stabilizing groups may include thiophenyl ($C_6H_5S$—), sulfinylphenyl ($C_6H_5SO$—), sulfonylphenyl ($C_6H_5SO_2$—), other thioaryl sulfinylaryl, and sulfonylaryl groups, and the like, and tertiary alkylthio groups. In a preferred embodiment, the anion stabilizing group is thiophenyl or sulfonylphenyl.

Y in Formula 4 above is hydrogen or lower-alkyl, preferably methyl, or ethyl. In a more preferred embodiment, Y is hydrogen or methyl.

Z in Formula 4 above is lower-alkoxy or phenylmethoxy. In a preferred embodiment, Z is selected from the group consisting of methoxy, ethoxy, n-propanoxy, and phenylmethoxy. In a more preferred embodiment, Z is methoxy or ethoxy.

M in Formula 4 above is a metal atom selected from the group consisting of alkali and alkaline earth metals. In a preferred embodiment, M is selected from the group consisting of lithium, sodium, and potassium. In a more preferred embodiment, M is lithium or sodium.

In a preferred embodiment, the anionic reagent of formula (4) is selected from the group consisting of the alpha-lithium derivatives of methoxymethyl phenyl sulfide, $C_6H_5SCHLiOCH_3$, and methoxymethyl phenyl sulfoxide, $C_6H_5SO_2CHLiOCH_3$, especially the former.

The Schiff base compound (3) may be selected from a wide variety of compounds to prepare compounds of type (I). Suitable compounds of type (I) are set forth below.

Reaction conditions suitable for carrying out the addition of the anionic reagent (4) to the Schiff base compound (3) are disclosed in, for example. V. H. Rawal et al., *Synthetic Communications.* 14, 1129-1139 (1984), which disclosure is incorporated herein by reference.

Suitable reducing agents in the present invention include Raney nickel, metal hydrides, and sodium amalgam. Suitable metal hydrides include n-tributyltin hydride and triphenyltin hydride. In a preferred embodiment, the reducing agent is a member selected from the group consisting of n-tributyltin hydride and triphenyltin hydride.

When the desired $R_2$ substituent group is not phenylethyl, one procedure for preparing compounds of the present invention with different $R_2$ groups is to begin with compounds of type (2) according to the following scheme:

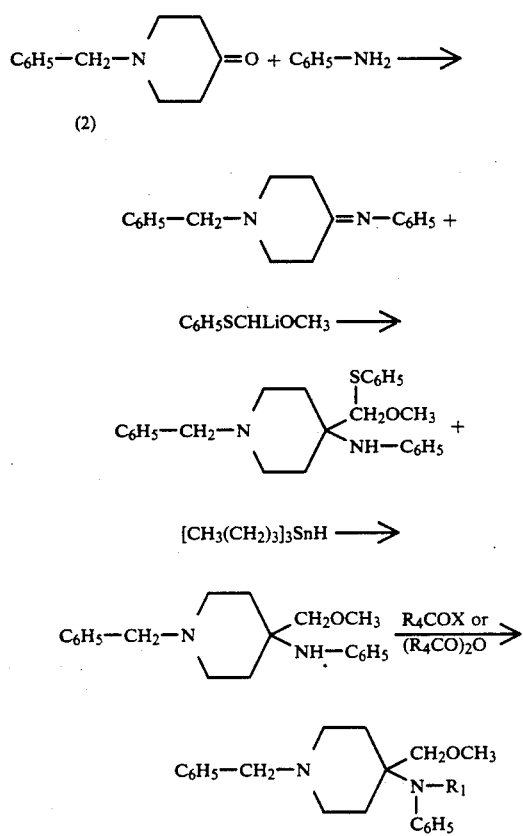

The phenylmethyl group in compound (7) can be removed by hydrogenolysis, or by reaction with 1-chlorethyl chloroformate followed by hydroysis with methanol. The preparation of secondary amines of type (8) has been described by P. G. H. Van Daele et al., *Arzneim-Forsch. Drug Res.*, 26, p. 1521, (1976) and R. A. Olofson et al., *J. Org. Chem.*, 49, pp. 2081-2082 (1984). The phenylmethyl group can be replaced with a desired $R_2$ substituent group by reacting compound (8) with an appropriately reactive molecule of the formula $R_2$—X, wherein X is halogen, such as chlorine, bromine, or iodine, or its reactive equivalent, such as toluene sulfonate, phenyl sulfonate, methyl sulfonate, and the like, to obtain compound (I) according to the reaction scheme illustrated below:

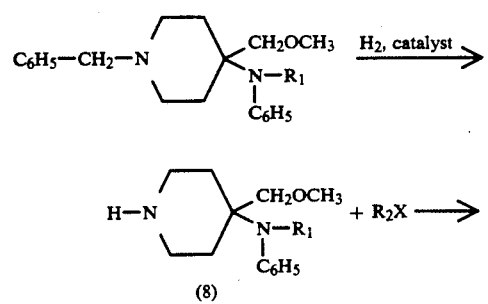

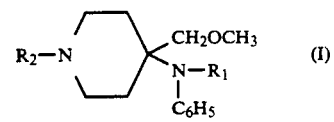

The reaction of $R_2$—X with a piperidinyl intermediate of type (8) can be conducted in an inert organic solvent such as, for example, an aromatic hydrocarbon, a ketone such as 4-methyl-2-pentanone and the like, an ether such as 1,4-dioxane, diethylether, tetrahydofuran, 1,2-dimethoxyethane and the like, or N,N-dimethylformamide. The addition of an appropriate base, such as an alkali metal carbonate, may be utilized to neutralize the acid generated during the reaction. The addition of an iodide salt, such as an alkali metal iodide, may be appropriate. The temperature of the reaction mixture may be raised to increase the rate of reaction when appropriate.

The compounds which may be prepared by the method of the present invention possess very desirable analgesic activities. In particular, these compounds produce central nervous system depressant effects including analgesia, hypnosis, sedation, increased pain threshold, and barbiturate and/or general anesthetic potentiation. Many of the compounds provide highly potent analgesia with an immediate onset and short duration of activity. These properties are highly desirable in circumstances where acute pain must be eliminated over a short period of time, such as in anesthesiology. Preferred compounds prepared by the subject method provide reduced rigidity at high doses, superior motor coordination recovery, or less respiratory depressive and/or cardiovascular depressive activity when compared to fentanyl, i.e. N-phenyl-N-[1-(2-phenylethyl)-4-piperidinyl] propanamide.

In the compounds of formula I above prepared by the subject method, R is phenyl or substituted phenyl, wherein the substituents are independently selected from the group consisting of hals, lower-alkyl, lower-alkoxy, and combinations thereof. Preferred substituents are fluoro and methoxy. The preferred position for attachment of a substituent to the phenyl ring is at the 2 (ortho) position. In a preferred embodiment, R is selected from the group consisting of phenyl, 2-fluorophenyl and 2-methoxyphenyl.

Group $R_1$ in formula I above is selected from the group consisting of hydrogen, lower-alkyl carbonyl, lower-alkenyl carbonyl, lower-alkoxy, lower-alkyl, carbonyl and cycloalkyl carbonyl, each alkyl group having from 1 to 6 carbon atoms. In a preferred embodiment, the $R_1$ group is a member selected from the group consisting of ethyl carbonyl, ethenyl carbonyl, methoxy methyl carbonyl and alpha-methoxy ethyl carbonyl.

Group $R_2$ in formula I above is selected from the group consisting of hydrogen, lower-alkyl, lower cycloalkylmethyl, phenyl lower-alkyl, and heterocyclic ring system lower-alkyl. The phenyl lower-alkyl group may be unsubstituted or substituted, wherein the substituents on the phenyl ring are selected from the group consisting of halogen, lower-alkoxy, lower-alkyl and combinations thereof. The heterocyclic lower-alkyl ring systems may be selected from the group consisting of monocyclic heterocyclic lower-alkyl ring systems having 5 to 6 ring member atoms and fused bicyclic and tricyclic heterocyclic lower-alkyl ring systems having 5 to 6 ring member atoms in each ring of the polycyclic ring system. Heteroatoms in the ring systems are selected from the group consisting of nitrogen, sulfur and oxygen.

The heterocyclic ring may be unsubstituted or substituted, with one or more substituents independently selected from the group consisting of halo, oxo, hydroxyl, nitro, amino, lower-alkoxy carbonyl, lower-alkyl, lower-cycloalkyl, lower-alkoxy, lower-mercaptoalkyl halogenated lower-alkyl, aryl, halogenated aryl, heterocycles, and combinations thereof. In a preferred embodiment, the substituents are selected from the group consisting of fluoro, chloro, iodo, oxo, nitro, amino, carbonyl, ethoxy carbonyl, methyl, ethyl, isopropyl, methoxy, mercaptomethyl, trifluoromethyl, phenyl, morpholinyl and combinations thereof.

The lower-alkyl group is selected from the group consisting of branched- or unbranched-hydrocarbon groups containing from 1 to 7 carbon atoms. The lower-alkyl group may be substituted or unsubstituted, with substituent members independently selected from the group consisting of oxygen, hydroxyl, sulfur, and combinations thereof. In a preferred embodiment, the lower-alkyl group is a member selected from the group consisting of methyl, ethyl, 2-hydroxyethyl, 2-oxoethyl, and 2-mercaptoethyl.

In a preferred embodiment, the heterocyclic lower-alkyl ring system is selected from the group consisting of pyrrolyl lower-alkyl, pyrazolyl lower-alkyl, imidazolyl lower-alkyl, imidazolinyl lower-alkyl, imidazolyl lower-thioaklyl, triazolyl lower-alkyl, triazolyl lower-thioalkyl, tetrazolyl lower-alkyl, tetrazolyl lower-thioalkyl, thienyl lower-alkyl, thienyl lower-oxyalkyl, thienyl lower-hydroxy-alkyl, furanyl lower-hydroxyalkyl, thiazolyl lower-alkyl, oxazolyl lower-alkyl, thiadiazolyl lower-alkyl, oxadiazolyl lower-alkyl, pyridin-1-yl lower-alkyl, pyridin-3-yl lower-alkyl, pyridin-4yl lower-alkyl, triazinyl lower-alkyl, pyrimidinyl lower-alkyl, pyridazinyl lower-alkyl, triazinyl lower alkyl, indolyl lower-alkyl, benzoxazolyl lower-alkyl, benzopyranyl lower-alkyl, benzodioxanyl lower-alkyl, benzothiazinyl lower-alkyl, quinazolinyl lower-alkyl, purinyl lower-alkyl, phthalimidyl lower-alkyl, naphthalenecarboxamidyl lower-alkyl, and naphthalenesulfamidyl lower-alkyl.

In a more preferred embodiment, the heterocyclic lower-alkyl ring system is selected from the consisting of thiazolyl lower alkyl, which can be substituted in the 4-position of the thiazalyl ring with a lower-alkyl group, 4,5-dihydro-5-oxo-1H- lower alkyl, which can be substituted in the 4-position of the tetrazal-1- yl ring with a lower-alkyl group, and thienyl lower-alkyl.

Group $R_3$ in formula I above is lower-alkoxy lower-alkyl or phenyl-methoxy lower-alkyl. In a preferred embodiment, $R_3$ is selected from the group consisting of methoxy methyl, ethoxy methyl, methoxy ethyl and ethoxy ethyl. In a more preferred embodiment, $R_3$ is methoxy methyl.

In a most preferred embodiment, the invention is directed to a method for preparing certain opioid N-phenylamino-N-(4-alkoxyalkylpiperidin-4-yl)amide derivatives having the general formula (I) wherein R is unsubstituted phenyl, $R_1$ is ethyl carbonyl, $R_2$ is 2-(2-thienyl)ethyl or 2-(4-ethyl-4,5-dihydro-5-oxo-1H- tetrazol-1yl)ethyl, and $R_3$ is methoxymethyl.

The term "lower-alkyl," as used herein, means branched- or unbranched-hydrocarbon groups containing from 1 to 7 carbon atoms, preferably from 1 to 4 carbon atoms. The definition applies as well to the alkyl portion of lower-alkoxy groups as used herein. The term "lower-thioalkoxy," as used herein, means branched- or unbranched-hydrothiocarboxy groups containing from 1 to 7 carbon atoms, preferably from 1 to 4 carbon atoms. The term "lower-cycloalkyl," as used herein, means cyclic alkyl groups containing from 3 to 6 carbon atoms. The term "halogen", as used herein, refers to the chemically related elements consisting of fluorine, chlorine, bromine and iodine, preferably fluorine.

The compounds of formula (I) which have at least one asymmetric carbon atom can exist in optically active isomeric forms. For example, in compounds in which $R_2$ is a 2-phenyl-1-propyl or 1-phenyl-2-propyl group, etc., the carbon adjacent to the piperidinyl nitrogen is an asymmetric carbon atom and such compounds can therefore exist in optical active isomeric (enantiomeric) forms. Such isomeric forms can be isolated from the racemic mixtures by techniques known to those skilled in the art.

The present invention is further illustrated by the following examples which are presented for purposes of demonstrating, but not limiting, the preparation of the compounds of this invention.

EXAMPLE 1

4-Phenylamino-4-(1-thiophenyl-1-methoxy-methyl)-N-phenylmethyl piperidine

This Example illustrates a method for preparing a Schiff base compound and the subsequent reaction of the Schiff base compound with an anionic reagent to prepare an intermediate compound according to the present invention.

A solution of N-phenylmethyl-4-piperidone (3.78 g, 20 mmole), aniline (1.87 g, 20 mmole) and p-toluenesulfonic acid (100 mg) in benzene (50 ml) was heated to reflux in a two-neck flask fitted with a Dean-Stark water trap overnight. The resulting reddish brown reaction solution was then concentrated under vacuum and the Schiff base residue was dissolved in anhydrous tetrahydrofuran (50 ml).

A solution of tert-butyllithium (24 mmole) in pentane was added dropwise to a solution of methoxymethyl phenyl sulfide (3.70 g, 24 mmole) in anhydrous tetrahydrofuran (100 ml) at −78° C. After addition, the resulting yellowish reaction solution was stirred for 1 hour at −78° C. The above Schiff base solution was added dropwise to the stirred lithium solution at −78° C. The resulting reaction solution was stirred at −78° C. for 15 minutes and then at room temperature for 20 minutes. The reaction solution was then quenched by adding $H_2O$ (100 ml). The resulting mixture was extracted with ethyl acetate (2×100 ml) and the combined organic layers were dried over sodium sulfate and concentrated under vacuum. The residue was chromatographed (silica gel; eluted with methylene chloride, then ethyl acetate/hexane, 1:3) to yield the product, 4-phenylamino-4-(1-thiophenyl-1-methoxymethyl)-N-phenylmethyl piperidine, (5.35g, 12.8 mmole), in 64% yield as an amber oil.

EXAMPLE 2

4-Phenylamino-4-methoxymethyl-N-phenylmethyl piperidine

This Example illustrates a method for displacing the thiophenyl anion stabilizing group in the intermediate compound of Example 1 to prepare a compound according to the present invention.

Raney nickel (38 g, wet, W-2, washed with ethanol, then ethyl acetate) was added to a solution of 4-phenylamino-4-(1-thiophenyl-1-methoxymethyl)-N-phenyl-methyl piperidine (3.10 g, 7.4 mmole) in ethyl acetate (100 ml). The resulting mixture was stirred at room temperature for 1 hour, filtered through a sintered glass funnel and the filtrate concentrated under vacuum. The resulting residue was chromatographed (silica gel; ethyl acetate) to yield the product, 4-phenylamino-4-methoxymethyl-N-phenylmethyl piperidine, (1.27 g, 4.1 mmole) in 55% yield as a colorless oil.

EXAMPLE 3

4-Phenylamino-4-methoxymethyl-N-phenylmethyl piperidine

This Example illustrates another method for displacing the thiophenyl anion stabilizing group in the intermediate compound of Example 1 to prepare a compound according to the present invention.

A 5 liter, 3-neck round bottom flask affixed with a thermometer, a magnetic stirrer, and a condenser connected to a dry nitrogen gas inlet tube was charged with 89.7 g (0.214 moles) of 4-phenylamino-4-(thiophenylmethoxymethyl-N-phenylmethyl piperidine, 3.0 g (18 mmoles) of azobisisobutyronitrile, 1.2 liters of toluene, and 307.1 g (1.023 moles) of n-tributylyin hydride. The reaction mixture was slowly heated to reflux over a period of 1 hour and then maintained at this temperature for 22 hours. The reaction mixture was quenched by the addition of a solution of 50 ml of concentrated hydrochloric acid and 50 ml of methanol at a temperature from about 0° C. to about 5° C. The mixture was made alkaline by the addition of 20% sodium hydroxide solution (250 g). The emulsified aqueous layer was extracted with toluene (3×150 ml). The combined organic layers were washed with water (2×150 ml), then dried over sodium sulfate, and concentrated under vacuum. The resulting residue was purified by column chromatography (silica gel; ethyl acetate/hexane, 1:9 to 1:1) to yield 56.5 g (81.8% yield) of the product, 4-phenylamino-4-methoxymethyl-N-phenylmethyl piperidine.

COMPARATIVE EXAMPLE

This Example illustrates the preparation of 4-alkyl-4-anilinopiperidines from N-(1-benzyl-4-piperidylidene)aniline essentially following the procedures of Janssen, U.S. Pat. No. 3,164,600 and utilizing n-butyl-lithium, methyllithium and methoxymethyllithium, respectively.

N-(1-benzyl-4-piperidylidene)aniline

A 1000 ml round bottom flask affixed with a stirring bar, a Dean-Stark trap and a condenser was charged with 101.6 g of benzylpiperidone, 500 ml of toluene, 50 g of aniline and 500 mg of p-toluene sulfonic acid. The mixture was refluxed overnight. After removal of the solvent, the reaction mixture was poured into 600 ml of isopropyl ether. The resulting solution was filtered, and the filtrate concentrated and then vacuum distilled at 185°–190° C., 1.25 torr to obtain 91.9 g (about 65% yield) of product as a light yellow oil.

1-Benzyl-4-n-butyl-4-anilinopiperidine

A dry 100 ml round bottom flask affixed with a stirring bar was charged with 30 ml of hexane to which was added through a syringe 4.4 ml of 2.5 M n-butyllithium (Aldrich Chemical). To the resulting solution which had been cooled to 0° C., was added a solution of 2.64 g (10 mmol) of the N-(1-benzyl-4-piperidylidene)aniline formed above in 15 ml of hexane via a syringe over about 5 minutes. An off-white precipitate formed during the additions. The reaction mixture was refluxed for 19 hours, cooled to room temperature and quenched with 1.5 ml of water. The resulting organic layer was separated, dried over sodium sulfate and concentrated to yield 2.8 g of crude product. The product was chromatographed through a silica column using a 5:1 mixture of hexane and ethyl acetate as the solvent. There was recovered 500 mg of product (15.5%) and 734 mg of benzyl piperidone.

This experiment was repeated using double the equivalents of N-butyl-lithium (8 ml of 2.5M). There was obtained 754 mg of product (23.4% yield) and 445 of benzyl piperidone.

1 1-Benzyl-4-methyl-4-anilinopiperidine

The reaction was run in a similar manner using 1.1 equivalents of methyllithium (7.85 ml. of 1.4M, Aldrich Chemical). There was obtained 222 mg of product (7.7% yield) and 1.07 g of benzyl piperidine.

Repeating the experiment with 2.0 equivalents (14.28 ml of 1.4M) methyllithium produce 388 mg of product (14.4%) and 815 mg of benzyl piperidone.

1-Benzyl-4-methoxymethyl-4-anilinopiperidine

Methoxymethyllithium was formed by the procedure disclosed in *Tetrahedron Letters*, Vol. 24, No. 31, (1983) pp 3163–3164, and the entire reaction was carried out in one reaction vessel.

A 250 ml round bottom flask was charged with a solution of 2.08 g stannous chloride in 60 ml of anhydrous tetrahydrofuran. This solution was treated with a 2M solution of lithium bromide, 905 mg in 6 ml of tetrahydrofuran, followed by 1.37 g (0.89 ml) of bromoacetone. The resulting solution was stirred for 30 minutes, cooled to −70° C. in an acetone/dry ice bath and treated by the dropwise addition of 17.6 ml of 2.5M n-butyllithium. The solution was stirred for 1 hour, then treated with 2.64 g of N-(1-benzyl-4-piperikylidene)aniline in 15 ml of hexane and stirred for 30 minutes, all at constant temperature. The mixture was allowed to warm to room temperature, refluxed overnight, cooled to room temperature and quenched with water. The organic layer was separated, dried and chromatographed as described above to yield 20 ml (0.6% yield) of product.

Utilizing 2.0 equivalents of methoxymethyllithium, as was done with the other lithium reactants, increased the yield to 3.2%.

The yields of all 4-alkyl-4-anilino-piperidines formed are considered unacceptably low.

It will be understood that the embodiments described herein are merely exemplary and that a person skilled in the art may make many variations and modifications without departing from the spirit and scope of the invention. All such modifications and variations are intended to be included within the scope of the invention as defined in the appended claims.

We claim:

1. A method for preparing a 4-alkoxyalkyl-4-phenylaminopiperidine compound having the general formula:

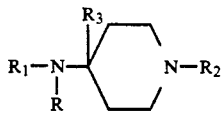

(I)

wherein
- R is selected from the group consisting of phenyl and substituted phenyl wherein the substituents are one or more members selected from the group consisting of halo, lower-alkyl and lower-alkoxy;
- $R_1$ is selected from the group consisting of hydrogens, lower-alkyl carbonyl, lower-alkenyl carbonyl, lower-alkoxy lower-alkyl carbonyl and cycloalkyl carbonyl;
- $R_2$ is selected from the group consisting of hydrogen, lower-alkyl, cycloalkylmethyl, phenyl lower-alkyl, pyrrolyl lower-alkyl, pyrazolyl lower-alkyl, imidazolyl lower-alkyl, imidazlinyl lower-alkyl, imidazolyl lower-thioalkyl, triazolyl lower-alkyl, triazolyl lower-thioalkyl, tetrazolyl lower-alkyl, tetrazolyl lower-thioalkyl, thienyl lower-alkyl, thienyl lower-oxyalkyl, thienyl lower-hydroxyalkyl, furnayl lower-hydroxyalkyl, thaizolyl lower-alkyl, oxazolyl lower-alkyl, thiadiazolyl lower alkyl, oxadiazolyl lower-alkyl, pyridin-1-yl lower-alkyl, pyridin-3-yl lower alkyl, pyridin-4-yl lower alkyl, piperidinyl lower-alkyl, pyrimidinyl lower-alkyl, pyridazinyl lower-alkyl, triazinyl lower-alkyl, indolyl lower-alkyl, isoidolyl lower-alkyl, benzimidazolyl lower-alkyl, benzopyrazolyl lower-alkyl, benzoxazolyl lower-alkyl, benzopyranyl lower-alkyl, benzodioxanyl lower-alkyl, benzothiazinyl lower-alkyl, quinazolinyl lower-alkyl, purinyl lower-alkyl, phthalimidyl lower-alkyl, napthalenecarboxamidyl lower-alkyl, and napthalenesulfamidyl lower-alkyl wherein the heterocyclic groups can be unsubstituted or substituted with one or more substituents selected from the group consisting of halo, oxo, hydroxyl, nitro, amino, lower-alkoxy carbonyl, lower-alkyl, lower-cycloalkyl, lower-alkoxy, mercaptolower alkyl, halogenated lower-alkyl, aryl, halogenated aryl, and a heterocyclic group;

and $R_3$ is methoxymethyl, which comprises:
- (a) reacting an N-$R_2$-substituted-4-piperidone compound with an aniline compound to form a Schiff base compound;
- (b) reacting the Schiff base compound with the alphalithium derivative of methoxymethyl phenyl sulfide to form an amine compound; and
- (c) reducing the amine compound.

2. The method according to claim 1, wherein said amine compound is reduced in step (c) with a reducing agent selected from the group consisting of Raney nickel, metal hydrides, and sodium amalgam.

3. The method according to claim 2, wherein the reducing agent is a member selected from the group consisting of n-tributyltin hydride and triphenyltin hydride.

4. The method according to claim 1, wherein R is phenyl; $R_1$ is ethyl carbonyl; $R_2$ is a member selected from the group consisting of 2-(2-thienyl)ethyl and 2-(4-ethyl-4,5-dihydro-5-oxo-lH-tetrazol-1-yl) ethyl.

5. The method according to claim 1, wherein $R_2$ is phenylmethyl or 2-phenyl ethyl.

6. The method according to claim 1, wherein R is selected from the group consisting of phenyl, 2-fluorophenyl and 2-methoxyphenyl; $R_1$ is selected from the group consisting of ethyl carbonyl, ethenyl carbonyl methoxy methyl carbonyl and methoxy ethyl carbonyl.

* * * * *